United States Patent [19]
Vanderlaan et al.

[11] Patent Number: 5,429,925
[45] Date of Patent: Jul. 4, 1995

[54] METHOD FOR IMMUNODIAGNOSTIC DETECTION OF DIOXINS AT LOW CONCENTRATIONS

[75] Inventors: Martin Vanderlaan, Danville; Larry H. Stanker; Bruce E. Watkins, both of Livermore, all of Calif.; Peter Petrovic, Hochheim am Main; Siegbert Gorbach, Eppstein/Ts., both of Germany

[73] Assignee: The Regents of the University of California, Oakland, Calif.

[21] Appl. No.: 966,565

[22] Filed: Oct. 26, 1992

Related U.S. Application Data

[63] Continuation of Ser. No. 335,692, Apr. 10, 1989, abandoned, which is a continuation-in-part of Ser. No. 237,192, Aug. 29, 1988, abandoned.

[30] Foreign Application Priority Data

Jan. 26, 1988 [DE] Germany .................. 38 02 157.9

[51] Int. Cl.$^6$ .............. G01N 33/53; G01N 33/535; G01N 33/537; G01N 33/543
[52] U.S. Cl. .................................... 435/7.1; 435/7.9; 435/7.92; 435/803; 435/961; 435/962; 435/7.5; 436/523; 436/531; 436/825; 436/815; 436/161
[58] Field of Search .............. 435/7.1, 7.9, 7.92, 435/803, 961, 962; 436/523, 531, 825, 815, 161

[56] References Cited

U.S. PATENT DOCUMENTS 4,238,472  12/1980  Albro et al. ....................... 424/1
4,798,807  1/1989  Vanderlaan et al. ............... 436/548
4,803,170  2/1989  Stanton et al. .................... 436/518

OTHER PUBLICATIONS

Butler, E. T., Antibody-Antigen and Antibody-Hapten Reactions, Enzyme-Immunoassay, E. T. Maggio, editor, CRC Press, Inc. (1980) 5–52.
Goetz, R., et al., Determination of Polychlorinated Dibenzo-p-dioxins and Dibenzofurans in Soil and Other Solid Environmental Samples, Chem. Abstract, (1989) 98:138860k.
Guesdon, J. L., The Use of Avidin-Biotin Interaction in Immunoenzymatic Techniques, J. Histochem. Cytochem. (1979) 2:1131–1139.
Kennel, S. J., et al., Monoclonal Antibody to Chlorinated Dibenzo-p-dioxins, Toxicol. Appl. Pharmacol. (1986) 82:256–263.
Rappe, C., Analysis of Polychlorinated Dioxins and Furans, Environ. Sci. Technol. (1984) 18:79A–90A.
Siddle, K., Properties and Applications of Monoclonal Antibodies, Alternative Immunoassays, W. P. Collins, editor, John Wiley & Sons, Ltd., (1985) 13–37.
*Principles of Biochemistry*, 7th Ed., E. Smith et al, eds., McGraw Hill Book Company, New York, N.Y., 1983, pp. 156–161.
Vanderlaan et al., "Immunochemical Quantification of Dioxins in Industrial Chemicals and Soils" (1988) LLNL Report UCRL-98223, Abstract.
Watkins, et al. "An Immunoassay for Chlorinated Dioxins in Soil" (1988), LLNL Report UCRI-98736.
Vanderlaan et al., "Improvement and Application of an Immunoassay for Screening Environmental Samples for Dioxin Contamination": (1988) *Environ. Toxicol. Chem.* 7: 859–870.
Vanderlaan et al., "Monoclonal Antibodies for the Detection of Trace Chemicals" (1987), Pesticide Science and Biotechnology, pp. 597–602.
Vanderlaan et al., "Environmental Monitoring by Immunoassay" (1988), *Environ. Sci. Technol.* 22(3): 247–254.
Oellerich, M., J. Clin. Chem. Clin. Biochem. vol. 22, 1984, pp. 895–904.

*Primary Examiner*—Toni R. Scheiner
*Attorney, Agent, or Firm*—Hana Dolezalova

[57] ABSTRACT

A method is described for the use of monoclonal antibodies in a sensitive immunoassay for halogenated dioxins and dibenzofurans in industrial samples which contain impurities. Appropriate sample preparation and selective enzyme amplification of the immunoassay sensitivity permits detection of dioxin contaminants in industrial or environmental samples at concentrations in the range of a few parts per trillion.

14 Claims, 2 Drawing Sheets

METHOD FOR IMMUNODIAGNOSTIC DETECTION OF DIOXINS AT LOW CONCENTRATIONS

The U.S. Government has rights in this invention pursuant to Contract No. W-7405-ENG-48 between the U.S. Department of Energy and the University of California, for the operation of the Lawrence Livermore National Laboratory.

CROSS REFERENCE

This is a continuation of application Ser. No. 07/335,692 filed Apr. 10, 1989, now abandoned which is a CIP of application Ser. No. 07/237,192, filed Aug. 29, 1988, now abandoned, and claims priority to application Ser. No. P 38 02 157.9, filed in the Federal Republic of Germany on Jan. 26, 1988, now pending.

FIELD OF THE INVENTION

This invention relates to an improved method for the detection of dioxins and dibenzofurans, using monoclonal antibodies and a method of sample preparation to optimize detection of dioxins by immunoassay in contaminated samples.

BACKGROUND OF THE INVENTION

Polychlorinated dibenzodioxins (PCDD) and dibenzofurans (PCDF) are persistent, toxic pollutants which pose a threat to both human health as well as the biosphere generally. These compounds, which may also be referred to as polyhalogenated planar polycyclic aromatics, are contaminants of herbicides, such as Agent Orange, and are generated as by-products in a variety of industrial chemical processes, as well as in the course of combustion or incineration of other polychlorinated organics, such as plastics and polychlorinated biphenyls (PCB). In view of the extensive use or occurrence of such processes, dioxins and dibenzofurans are widespread in the environment. Now that the harmful nature of these materials has become recognized, it has become a matter of high priority to address the issue of detection of these compounds. An important, nontrivial first step is to identify sites of pollution, which requires a simple, economical, and rapid test for detection of the presence of these compounds in samples taken from industrial processing, soils, human or animal tissues, as well as foodstuffs.

Polychlorinated dibenzodioxins (PCDDs) and dibenzofurans (PCDFs), and other chemicals formed during combustion and technical processes are extremely toxic and additionally environmentally stable. Efforts to monitor their formation and distribution have primarily been carried out by means of gas chromatography with mass spectroscopy, a relatively expensive procedure which involves elaborate sample preparation and the use of costly, complicated technical equipment. There is a need for a simpler and more economical analytical procedure for the substances mentioned, particularly those found in industrial samples which contain other substances which may interfere with the assay.

An important aspect of a desirable test procedure relates to specificity. There are a large number of congeners of both PCDDs and PCDFs, as well as PCBs, which vary in toxicity from very highly toxic to lesser toxicities, but which are also chemically similar to other, relatively harmless compounds. A second aspect of the problem is that the most toxic congener of these compounds in the environment, i.e., 2,3,7,8-tetrachlorodibenzo-p-dioxin (2,3,7,8-TCDD), is harmful in very small amounts, and is capable of being concentrated as it moves through food chains. Hence, a desirable test must be capable of detecting the presence of these harmful substances in very low concentrations in industrial process samples, environmental samples, human or animal tissues and foodstuffs. Chemical analysis of soil samples for contamination is also hampered by several other factors: (1) dioxins bind tightly to soil and show negligible solubility in water, and (2) the multiplicity of congeners and related chemical contaminants make quantitative assay by conventional gas chromatographic and mass spectrometric methods costly and time consuming. The costs and turn-around time of assays preclude detailed sampling of an area to determine the extent of contamination, and require the use of sophisticated centralized laboratories, unsuited for field monitoring of hazardous polychlorinated dibenzodioxins and dibenzofurans.

The present invention relates to a method of preparation of samples containing dioxins and related compounds such that they are suitable for assay by immunodiagnostic methods and a test kit which is useful for this procedure. Important members of the class of polyhalogenated polycyclic aromatics with a planar structure cited are dibenzodioxins, dibenzofurans and several polyhalogenated biphenyls. For purposes of simplification, the class of substances cited shall be referred to as dioxins or dioxin, when used as an adjective, as in dioxin fraction, in the following description.

DESCRIPTION OF THE RELATED ART

The potential advantages of immunoassay procedures over conventional analytic methods have been recognized previously, in particular, that an immunoassay procedure offers a method which is as sensitive as gas chromatography and/or mass spectrometry, while being more rapid and less expensive.

A previous approach to detection of dioxins in the environment has been the use of a radioimmunoassay, based on polyclonal antisera produced by the immunization of rabbits with 1-amino 3,7,8,-trichlorodibenzo-p-dioxin. That method was discussed in a paper by P. W. Albro et al in *Methods in Enzymology* 84:619–639 (1982) and U.S. Pat. No. 4,238,472. That assay has not been widely applied because it requires the frequent synthesis of $^{125}I$-TCDD substrate, it requires three days to complete, and because the assay uses non-specific rabbit antisera which is not sufficiently specific for the most toxic dioxin congener, 2,3,7,8-TCDD, hereinafter referred to as TCDD.

Another test for dioxins, reported by Stephen J. Kennel in a paper in *Toxicology and Applied Pharmacology*, 82: 256–263 (1986), is based on monoclonal antibodies produced by immunizing mice with thyroglobulin-2-adipamide, 3,7,8-trichlorodibenzo-p-dioxin has not proven specific for toxic dioxin compounds. Hybridomas produced by spleen cells of animals immunized with this compound and fused to myeloma cells secrete antibodies which have inadequate selectivity for nonprotein conjugated 2,3,7,8, tetrachlorodibenzo-p-dioxins. The test also uses a radioimmunoassay procedure with its attendant disadvantages.

Detection of dioxins discussed in recent publications describe immunoassays which employ monoclonal antibodies which bind specifically to toxic dioxins. The publications are: Stanker, L., Watkins, B., Rogers, N.

and Vanderlaan, M., "Monoclonal Antibodies to Dioxin, Antibody Characterization and Assay Development", Toxicol., 45:229-243 (1987); and Stanker, L., Watkins, B., Vanderlaan, M., and Budde, W., "Development of an Immunoassay for Chlorinated Dioxins Based on a Monoclonal Antibody and an Enzyme Linked Immunosorbency Assay (ELISA)", Chemosphere 16:1635-1639 (1987)). Chemically pure dioxins, or samples from which the dioxin may be readily isolated, can be readily analyzed by those procedures, however, samples from industrial processes, which contain other substances which may be interactive with the assay, were not tested. Until this invention, procedure for analysis of industrial and environmental samples has not been available because of difficulties which are encountered during sample preparation which require partial purification of the dioxin fraction and then solubilization of the dioxin fraction into an aqueous solution for specific antibody detection. The procedure herein described enables the use of immunodiagnostic assay of dioxins in samples which may contain interfering contaminants of chemical processing or environmental samples.

Previous investigators have used various preparative extraction and chromatographic techniques for samples to be evaluated for dioxin contamination. These techniques are suitable for preparation of samples to be analyzed by gas chromatography/mass spectroscopy. It is unknown whether these samples may still have components which interfere with immunoassays. Preparative methods include Soxhlet extraction with phenol or toluene followed by multiple chromatographic treatment of samples for GC/LRMS analysis and alumina columns to partition dioxins from materials found in a hazardous waste storage site, although these methods gave a wide variation in results. All of these described procedures were used to prepare samples for GC/MS analysis. It was not determined whether those samples were free of substances which may interfere with antibody reactions which take place in an aqueous environment.

In a comparison of interlaboratory test reliability and sensitivity, it was determined that the practical limits of sample detection by GC/MS on samples prepared from technical grade products was about 10 ppb, with a reproducibility of $+/-100\%$. Application of the herein described method of sample preparation and analysis by means of monoclonal antibodies will yield a similar or better degree of detection and reproducibility.

To make the dioxin available to the antibodies for aqueous phase immunoassay procedures previously described used non-ionic detergents. These procedures indicated that only Triton X-305 and Cutscum ™ were suitable for the radioimmunoassay of dioxin, because other detergents did not solublize the TCDD. It was not distinguished whether these detergents would interfere in reactions using dioxin-specific monoclonal antibodies.

OBJECTS OF THE INVENTION

The foregoing clearly indicates that there exists a continuing need for an effective, practical test for detection of toxic dioxins.

Accordingly, a major object of this invention is to prepare samples from industrial or chemical processes for immunoassay of dioxins, such that the assay will have the necessary selectivity and sensitivity to conclusively indicate the presence of dioxins in concentrations of a few parts per billion (nanograms per sample).

Another objective is to provide a simplified extraction and detection test for dioxins which can be carried out rapidly in the field environment.

Yet another object is to provide an immunoassay capable of distinguishing the most toxic of the dioxins.

Another object is to define a procedure whereby sensitivity of dioxin detection can be raised to achieve detection at a few parts per trillion level.

Another object is to provide qualitative and quantitative determination of polyhalogenated polycyclic aromatics with planar structure, which are referred to as dioxins, in crude industrial and environmental samples, including soils.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is a method for preparation of samples for determination of the presence of polychlorinated dioxins and particularly 2,3,7,8-tetrachlorodibenzo-p-dioxin (TCDD), using monoclonal antibodies which are obtained from hybridoma cell lines. The production of the cell lines and characterization of the antibodies derived therefrom has been described in greater detail in U.S. Pat. No. 4,798,807 by Vanderlaan, et al. These antibodies are characterized by high affinity and selectivity toward TCDD. Their use with an improved ELISA test protocol (Enzyme-linked-Immunosorbent-Assay) permits the determination of the presence of dioxins in test samples at levels of a few parts per billion and less. Tests can be completed in hours rather than days. The use of radio-labeled compounds is obviated. Antibody tests for TCDD can be conducted in aqueous media with solubilization of the organic test compounds increased by detergents and/or sonication. In a preferred mode, the sensitivity of the immunoassay procedure can be raised through solubilization of the sample material by addition of detergents at a concentration on the order of about 0.01-2.0% by weight. Use of limited concentration of coating antigen and amplification of the peroxidase enzyme endpoint with an avidin/biotin amplification system makes it possible to detect TCDD concentrations in the range of a few parts per trillion. Other antibody preparations obtained using desired dioxins as immunogens can also be used.

The sample preparation procedures described herein enable sensitive analysis of industrial samples, which may include reaction mixtures, distillation residues, chemicals, fly ash, filter dust, transformer fluid (PCB oil) or motor oil. Additionally, the procedure may be employed for examination of samples of other origins, including environmental air, water and soil samples, human and animal tissues, and foodstuffs. The sample preparation procedure includes preliminary extraction and separation of the fraction containing the dioxin compounds of interest and subsequent solubilization of that fraction with detergents to expose the dioxin compounds to the aqueous immuno-assay reactants. Selection of an appropriate antigen coating concentration of the reaction vessel and selection of an enzymatic amplification system for the ELISA will further increase the sensitivity of the assay. The method is particularly suited for analytical determination of polychlorinated dibenzodioxins and dibenzofurans, and specific detection is effected into the range of a few parts per trillion.

DESCRIPTION OF THE INVENTION

Source of Antibodies

Figure 1A:
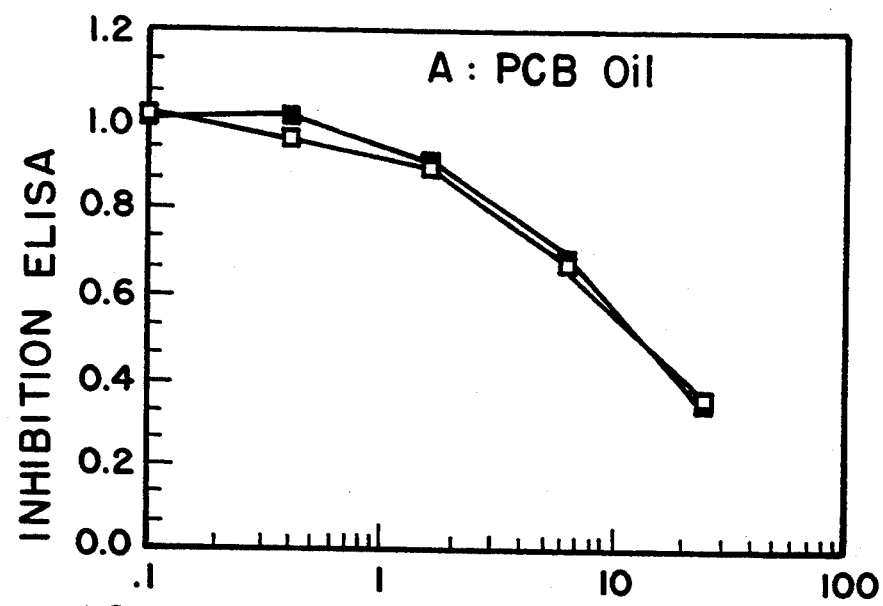
FIGS. 1A, 1B and 1C show Inhibition ELISA data for sample extracts prepared by clean-up of carbon column alone (open square) or carbon column followed by oleum-silica column, also referred to as a fuming sulfuric acid-silica column, (closed square). Additional sample extraction with fuming sulfuric acid-silica column did not alter $I_{50}$ on samples of PCB oil (1A) or trichlorophenol (1B), but the $I_{50}$ was lower for still bottom sample #1 (1C), a distillation residue from a chloronitrobenzene still, indicating that the second extraction was needed to remove non-dioxin, immunologically cross-reactive material.

The present method of sample preparation will produce samples which can be effectively analyzed for dioxins with monoclonal antibodies which are specific for polychlorinated dibenzodioxins (PCDD) and dibenzofurans (PCDF). Antibodies which were raised to discriminate the functional groups of dioxin molecules will have adequate specificity in the assay described herein.

Hybridomas which produce polyhalogenated planar polycyclic aromatic-specific antibodies, referred to as dioxin specific antibodies, are used. Illustrative are the named hybridomas, DD-1, DD-3, DD-4, DD-5, and DD-6, described by Vanderlaan, et al. in U.S. Pat. No. 4,798,807. These hybridomas are publicly available in the depository of the American Type Culture Collection (ATCC), Rockville, Md., and are identified with the following accession numbers: DD-1, (HB 9741); DD-3, (HB 9742); DD-4, (HB 9743); DD-5, (HB 9744); and DD-6, (HB 9745). These cells were produced by fusion of myeloma cells with spleenocytes obtained from a mouse immunized with the TCDD analog, 1-amino-3,7,8,-trichlorodibenzo-p-dioxin (A-triCDD). This compound was synthesized and then conjugated to bovine serum albumin carrier protein. After immunization with the hapten-protein complex, the immunoreactive spleen cells were collected and fused with myeloma cells, and the resulting hybridomas were screened for those with the ability to recognize TCDD, which was bound to protein and to free suspended TCDD. From these screenings, five hybridomas (named DD-1, DD-3, DD-4, DD-5 and DD-6) were selected for further study of their specificity. The specificity of these antibodies for a variety of dioxins, dibenzofurans, PCBs and other chlorinated hydrocarbons is reported by Vanderlaan, et al. in U.S. Pat. No. 4,798,807. The binding specificities of these antibodies are highly desirable, since they bind selectively to the most toxic of the dioxin and dibenzofuran isomers.

Sample Preparation

The analytical procedure suitable for industrial and environmental samples was developed to overcome problems of real world sample analysis by initiation of a partial purification and extraction of the toxic dioxins prior to their solubilization into aqueous solutions for immunoassay. The sample preparation procedure enables qualitative and quantitative determination of dioxin compounds in industrial samples of reaction mixtures, distillation residues and other heavily contaminated samples. Monoclonal antibodies specifically reactive with dioxins were described above (Stanker, et al (1987). *Toxicol.*, 45: 229–243). As individual antibodies may bind with certain compounds or groups of compounds, the results of several preparative schemes are best compared by relating to a standard compound of known concentration in a standard sample.

It is expedient to extract and/or prepare industrial samples before conducting the immunoassay reaction for determination of dioxins. This is preferably accomplished by the following consecutive steps:

a. Preparation of a raw extract,
 b. Separation of the fraction containing polyhalogenated polycyclic aromatics with a planar structure, referred to as the dioxin fraction,
 c. Transfer of the dioxin fraction into an aqueous buffer solution.

It is best to perform acid digestion prior to analysis of primarily inorganic samples such as fly ash, filter dust and inorganic chemicals. Various acids are suited to this end, in particular concentrated HCl or $H_2SO_4$ being preferred. Following acid treatment, the mixture is then extracted with an organic solvent or a mixture of solvents. Various organic solvents are suited to this end. The preferred solvents include $CCl_4$, $CHCl_3$, $CH_2Cl_2$, benzene, toluene, chlorobenzene, chlorotoluene, hexane, cyclohexane and chlorocyclohexanes. Especially preferred are $CH_2Cl_2$ and cyclohexane, in particular, mixtures of these two solvents.

Slightly soluble samples which are primarily organic in nature, such as reaction and distillation residues, are preferably prepared by suspending them in an acid, preferably concentrated $H_2SO_4$ saturated with $SO_3$, which is known as fuming sulfuric acid or oleum, and then mixing them with a solid (e.g. silica gel), preferably until the mixture becomes flowable. This mixture may subsequently be extracted at reflux in a suitable apparatus, preferably with one of the solvents cited above or with a corresponding mixture.

Readily soluble samples, which are primarily organic in nature, such as motor oil, PCB oil and organic chemicals, are advisedly dissolved, without previous acid treatment, in one or more of the solvents mentioned above.

The dioxin fraction may be separated in various ways from the extract obtained. To be preferred here is separation by means of a chromatographic procedure similar to that described by the Environmental Protection Agency in "Polyhalogenated Dibenzo-p-Dioxins/Dibenzofurans; Testing and Reporting Requirements. Federal Register, 52 : 108, Jun. 5, 1987, pp. 21412–21452, 40CFR parts 707 and 766. Especially preferred is separation by means of solid-liquid chromatography, for example with a solid phase consisting of glass fiber homogeneously mixed with active carbon. The glass fibers and the active carbon are advisedly blended (e.g., with a device having counter-rotating blades or with a mill) if necessary following the addition of a solvent. The content of active carbon measures about 5 to 15% by weight, with a preferred content of about 8–12%, especially about 10%, being preferred in particular.

The dioxin fraction is best separated with the latter method in a column procedure. To this end, the dioxin extract is applied to the column provided with a solid phase of glass fibers coated with active carbon. The column is washed following the application of the dioxin extract, if necessary, preferably with a mixture consisting of $CH_2Cl_2$ and hexane, with a mixture ratio of about 0.8 to 1.2 parts to about 0.8 to 1.2 parts being especially preferred. Another washing procedure with other solvents may follow, with a mixture consisting of dichloromethane, methanol and toluene being preferred, especially in a mixture ratio of about 65 to 85 : 15 to 25 : 0 to 10. Many other solvents and mixtures thereof are also suited for the washing procedures described. Preferred solvents are those which were already cited in connection with preparation of the extracts. The optimum composition of the washing liquids may have to be determined empirically for special extract compositions.

The dioxin fraction is preferably eluted by reversing the direction of solvent flow in the column and various solvents or mixtures thereof may be employed for this process. Preferred here is the application of toluene, benzene, xylenes and their chlorinated derivatives. Toluene is particularly preferred. The determination of suitable compositions for the washing and elution liquid may be simplified via experiments in which a marker dye is added to the dioxin extract. The marker dye (e.g., fat blue B (p-anthraquinone derivative manufactured by Hoechst AG, Frankfurt, FRG)) is adsorbed and eluted in a similar manner to the dioxin fraction in question. Marker dyes such as these are also suitable for monitoring the efficacy of individual washing steps of the elution process.

Figure 1B:
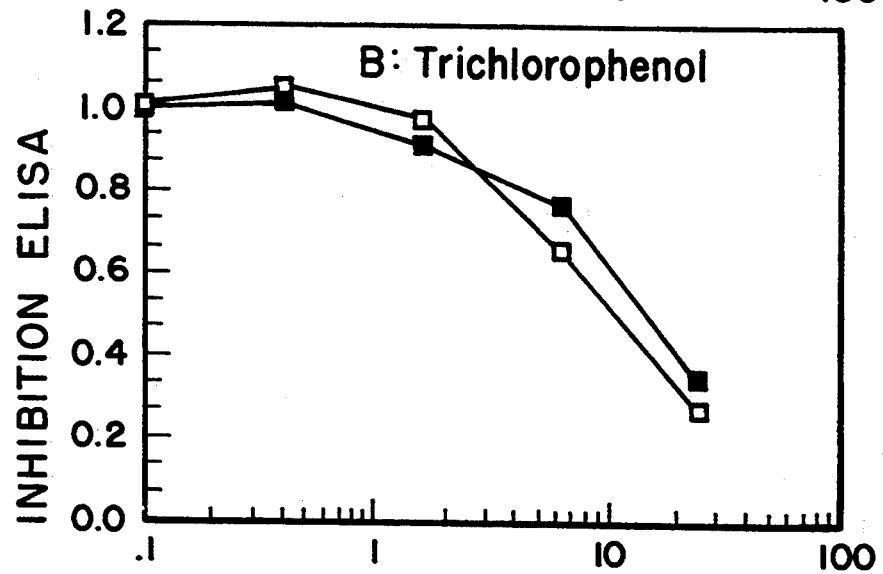
Figure 1C:
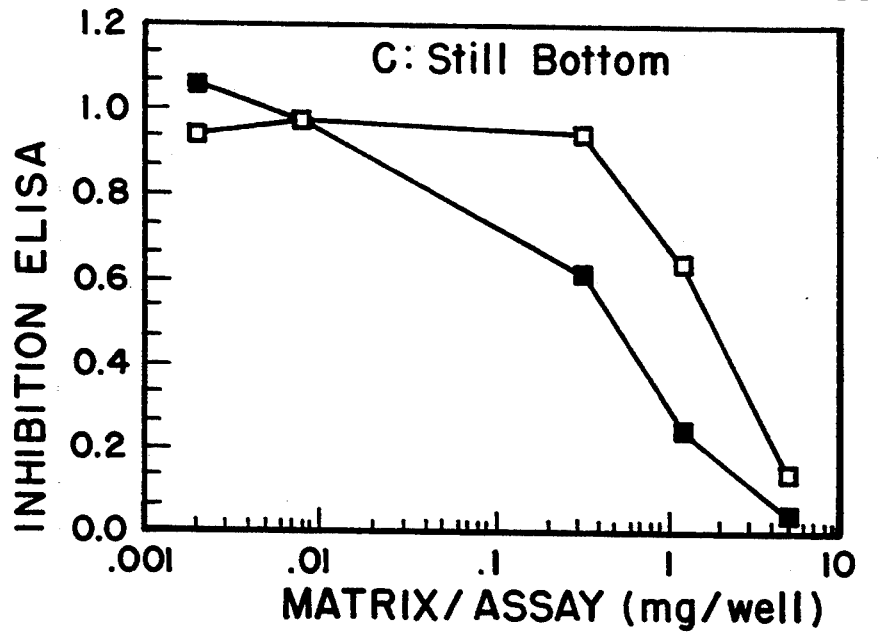

An additional cleansing operation may be used in exceptional cases where the dioxin fraction still contains interfering components after a single chromatographic wash. This may be another solid-liquid chromatographic extraction, for example. Chromatography using a column with acid-impregnated silica gel as the solid phase has been shown to be especially well suited. This column may be made by addition of about one part of $SO_3$-saturated $H_2SO_4$ to approximately 8 to 12 parts of fuming sulfuric acid-silica gel and heating this mixture for about 10 to 20 minutes to about 70°–90° C. The still impure dioxin fraction is added to one part of the acid impregnated silica gel, and this mixture is poured into a column as the uppermost layer. Additional layers consisting of about 5 to 15% $AgNO_3$ silica gel (obtained by mixing an aqueous $AgNO_3$ solution with silica gel and subsequently evaporating the water) and of fuming sulfuric acid-silica gel may be poured in. The layers should be separated from one another by silica gel or acid impregnated silica gel. The dioxin may be obtained from a column manufactured in the manner described via elution with a non-polar organic solvent such as hexane, cyclohexane, benzene and toluene, preferably hexane. The ELISA assay data of FIG. 1 illustrate that a second extraction with the fuming sulfuric acid-silica column did not alter the immunoassay analysis results following a single carbon column extraction for dioxin congeners in PCB transformer oil (panel A) or in trichlorophenol (panel B), but did remove non-dioxin, immunochemically cross-reactive material from the distillation residue of still bottom sample #1 (panel C). Radiolabeled dioxin was used to determine sample recovery efficiencies which were typically about 90%, with not less than 70% recovery.

The dioxin fraction obtained as per the method described is then assayed for the detection of dioxins by reaction with monoclonal or polyclonal antibodies. The immunoassay may be applied in various ways, for example as described in P. Tijssen, "Practice and Theory of Enzyme Immunoassays" (R. H. Burdon and P. H. Van Knippenberg, eds.) Elsevier, Amsterdam (1985). The immunoassay is preferably applied as a competitive assay. To this end, the concentrated dioxin fraction is best dissolved in an organic solvent or mixture of solvents, with non-polar organic solvents such as hexane and cyclohexane being particularly suited for these purposes. Advisedly added to this solution is an alcohol solution of detergents, preferably one or more nonionic surfactants such as isooctylphenoxypolyethoxyethanol, which was formerly sold as Cutscum TM by Fischer Scientific Company, Raleigh, N.C., U.S.A. and is now sold as Triton X-100 ® by Rohm & Haas, polyoxyethylene ethers such as polyoxyethylene stearyl ether or polyoxyethylene lauryl ether, N-octanoylglucopyranosides, N-heptylglucopyranosides, nonanoyl-N-methylglucamide, heptanoyl-N-methyl glucamide, polyoxyethylene sorbitan monolaurate, octyl-phenol ethoxylate, 3-(3-cholamidopropyl)-dimethylammonio- 2-hydroxy-1-propane sulfonate, 3-(3-cholamidopropyl)-dimethylammonio-1-propane sulfonate or octanoyl-N-methyl glucamide, with polyoxyethylene ethers such as polyoxyethylene stearyl ether and polyoxyethylene lauryl ether, polyoxyethylene sorbitan monolaurate, which is known as Tween TM, octylphenol ethoxylate, and isooctyl phenoxypolyethoxyethanol, which is known as Triton X-100 ®, being preferred, especially Triton X-100 ® or Tween TM.

Figure 2:
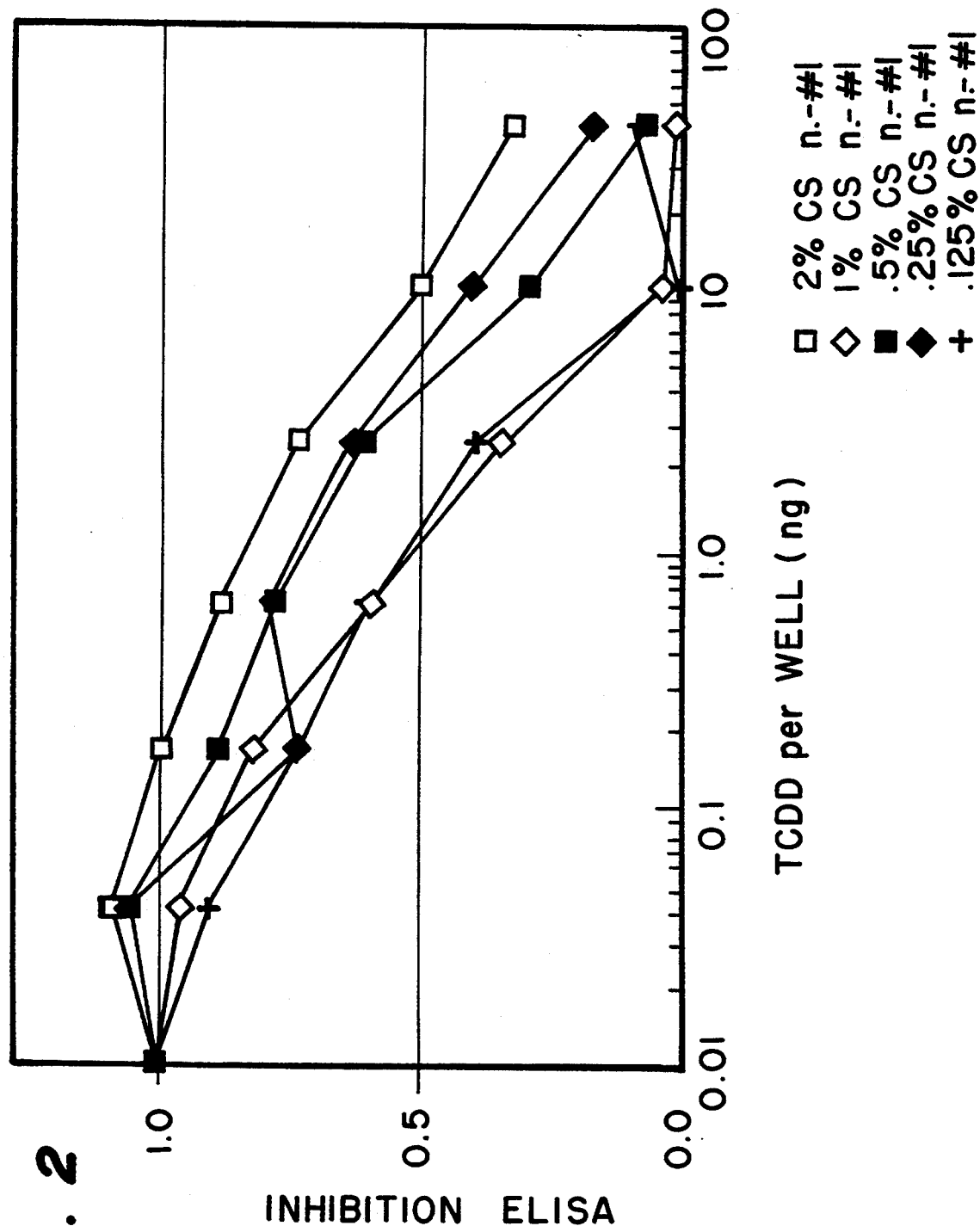
FIG. 2—Sensitivity of dioxin immunoassay is improved with detergent, Cutscum ™, solubilization of TCDD standard. Optimal assay sensitivity ($I_{50}$) is achieved with 0.25% (open diamond) and 0.125% (cross) Cutscum ™, whereas higher detergent concentrations, 0.5% (closed square); 1.0% (closed diamond) and 2.0% (open square) progressively inhibited competition. Detergent concentrations less than 0.1% failed to solubilize dioxin.

The detergents mentioned are preferably employed in a concentration of about 0.01 to about 2 percent by weight, with a preferred concentration of less than 1 percent by weight, especially of about 0.1 to 0.4 percent by weight, being preferred in particular. The effect of detergent concentration on immunoassay sensitivity is demonstrated in FIG. 2. The maximum effectiveness occured when the detergent concentration is at about 0.1 to 0.4 percent by weight. When the concentration of detergents is too high, the dioxin dissolves well but is no longer "recognized" by the antibody, which results in reduced sensitivity of the immunoassay. Sonication or ultrasonic mixing, will improve the solubilization of the dioxin fraction. This aqueous solution of detergents may also contain a portion of organic solvent such as acetone or methanol to ease pipetting.

The combined solutions are advisedly dried, for example, via a stream of nitrogen or warm air. The monoclonal antibody, which may be dissolved in an aqueous buffer solution, is subsequently added.

The aqueous buffer solution for suspension of the dioxin fraction is comprised of various substances. It preferably comprises the following: about 0.05 to 0.15 moles per liter of a compound or mixture of compounds buffering in a pH range of 7 to 8, with buffers based on tris(hydroxymethyl)-aminomethane or phosphate buffers being preferred in particular; about 0.1 to 5% by weight of a protein, especially about 0.2 to 1%, of a protein, preferably egg albumin, rabbit serum albumin or bovine serum albumin, with bovine serum albumin, especially preferred; about 0.1 to 0.3 moles per liter of an alkali halide, preferably NaCl; about 0.005 to 0.5% by volume of detergents, especially preferred 0.008 to 0.012 percent by volume of detergents, preferably one of the detergents mentioned above, in particular polyoxyethylene sorbitan monolaurate.

Immunoassay

The preferred vessel for execution of the competitive immunoassay is an antigen-coated test tube, preferably consisting of polystyrene, preferably in the form of a microtiter plate. The coating antigen may be applied in various ways, for example as described in the aforementioned monograph of R. Tijssen. Preferably employed is a solution of dioxin-protein conjugate consisting of polyhalogenated polycyclic aromatics having a planar structure, preferably dibenzodioxin or dibenzofuran, reacted with mammalian serum albumin, preferably rabbit or bovine serum albumin, with which the reaction vessel is treated.

After the coated vessel has been incubated with an antibody-dioxin mixture, the unbound material may be rinsed out and the bound antibody material detected in a known manner, for example by measurement of the labeling of the antibody. A radioactive isotope or compounds which may participate in a chemiluminescence or fluorescence emission in an enzyme-catalyzed reaction may be used for labeling. The larger the detected signal during the competitive assay, the lower the dioxin concentration in the tested sample. Previous operation of the assay demonstrated a practical limit of hapten detection when the amount of protein-hapten conjugate used was limited to 50 ng/well.

However, a preferred method for execution of the competitive immunoassay includes coating the immunoreactive wells with a limited amount of antigen, as less analyte is required to draw the antibody from the bound hapten. Optimal sensitivity of the detection system is obtained when the preferred concentration of the plating antigen is reduced from about 100 ng to about 0.5 ng of coating antigen per well, a concentration of between about 0.2 ng to 1.0 ng being especially preferred. To detect such a limited quantity of coating antigen, however, the signal must be additionally amplified. A preferred method of amplification of the enzyme-catalyzed optically-detected signal is with an avidin-peroxidase/biotin-anti-mouse immunoglobulin system which improves the sensitivity of the immunoassay when run with low background levels of plated antigen. The avidin-peroxidase/biotin-anti-mouse immunoglobulin system may be used to improve the efficacy of enzyme-linked immunoassay as the biotin can be easily coupled to antibodies or enzymes without loss of activity. The exceptionally high binding affinity of avidin ($10^{15}$/M) for biotin results in the formation of bridging complexes between biotinylated molecules. Both the specific-binding monoclonal antibody and the peroxidase-enzyme indicator system are bound to biotin. Linkage of the biotin molecules with avidin results in complexing of the indicator molecules and increases the sensitivity of the spectrally detectable signal.

Dioxin specific antibodies may be conjugated to biotin by the method described in Chapter 3 of the aforementioned P. Tijssen monograph. Biotinyl-N-hydroxysuccinimide (BNHS) ester can be allowed to react with the dioxin specific antibodies to make the biotinylated immunoreactants. In a preferred method, the dioxin-specific antibody can be identified by the binding of a biotinylated anti-mouse IgG immunoglobulin to the antibody. Biotinylated peroxidase, Vectastain (Vector Laboratories, Burlingame, Calif.) can be used as the detection signal after bridging to the avidin-biotin amplification complex.

A statement of the dioxin contamination of a sample may be made with a single analysis using the procedure described in this invention. In order to ensure a higher level of certainty of quantitative statements, however, it is best to measure a dilution series of the sample under examination, preferably with contemporaneous standard samples of known dioxin content.

A test kit can be assembled for execution of the reaction as per the invention which contains all necessary chemicals, such as chromatography material, solvents and eluents, test tubes, detergents, antibodies and chemicals for the detection reaction. Such a test kit should preferably be based on endpoint determination by fluorescence reaction or an enzyme-catalyzed reaction, because the outlay of equipment for the test reaction kit would then be economical and conveniently available for use in almost any laboratory.

EXAMPLE 1

Extraction Procedure

Dioxin content of a distillation residue of chlorinated aromatics may be examined with specific monoclonal antibodies following extraction and fractionation. A 5 g sample of distillation residue is suspended in 20 ml of $H_2SO_4$ saturated with $SO_3$ and mixed with silica gel until a flowable mixture is obtained. The mixture is extracted in a Soxhlet extractor with approximately 200 ml of boiling toluene. The extract is concentrated in a rotary evaporator and the extract and 1 mg of fat blue B are dissolved in 50 ml of dichloromethane/cyclohexane (50:50) and loaded into a column filled with 1 g of active carbon (10%) on glass fibers (63–200 $\mu$M size), which have been activated by drying at 130° C. for several hours. The column is washed with 50 ml of dichloromethane/cyclohexane (50:50) and 75 ml of dichloromethane/methanol/toluene (75:20:5). The column solvent flow is subsequently reversed and eluted in the opposite direction with 50 ml of toluene. The toluene eluate contains the "dioxin fraction" and is dyed blue. The toluene is removed by rotary evaporation and the residue is dissolved in 1 ml of n-hexane. The hexane solution is loaded on 2 g of acid impregnated-silica gel (1:10), which has also been activated by previous heating to 130 ° C., and mixed in the rotary evaporator for 15 minutes at 80° C. The sample which has adsorbed on the silica gel is loaded into a column already filled with 1 g of acid impregnated-silica gel (1:10), 1 g of silver nitrate/silica gel (1:10) and 0.5 g of silica gel between each layer. The column is eluted with 50 ml of n-hexane. The eluate containing the "dioxin fraction" is evaporated in the rotary evaporator, the residue dissolved in 500 ul of n-hexane and examined for dioxin content in the competitive immunoassay. By competitive immunoassay, the sample evaluated had a content of 2,3,7,8-TCDD equivalents measuring 25 ppb.

EXAMPLE 2

Immunoassay Procedure

The competition test procedure for dioxins has been discussed in detail by Stanker, el at. (1987) (Chemosphere 16: 1635–1639). A large part of the success of the instant method, which uses monoclonal antibodies with characterized binding specificity, is attributed to the development of a reliable competition ELISA protocol. Microtiter plates are coated with tri-CDD-albumin (antigen) solution, exposed to a blocking solution of albumin and then subjected to a dilution series of solubilized sample or dioxin standard. Sonication or ultrasonic mixing improves the solubilization of the dioxin fraction into the antibody solution. When the antibody solution is added, the antibody partitions between the tri-CDD-albumin (antigen) bound to the plate and to the dioxin sample in solution. After reaction, the sample solution is removed, and the plate is rewashed and incubated with an enzyme-tagged identification molecule. Development of the enzyme-antibody conjugate with appropriate substrate permits visualization of the monoclonal antibody which has bound to the tri-CDD-albumin (tricholorodibenzodioxin-albumin conjugate) or antigen, that is fixed to the plate. The results are then expressed as a fraction of the response in wells with no competitor. From such data, one can determine the concentration required to inhibit antibody binding by 50% ($I_{50}$).

For the immunoassay, which has been described by Stanker, et al (1987), the "dioxin fraction" is divided into five equal parts of 100 ul. Two parts remain unchanged, while one part is diluted six times at a ratio of 1:2, and two parts are spiked with 1 or 10 ng of 2,3,7,8-TCDD standard. Detergent solution, 40 ul of 0.5% Cutscum TM in acetone, is added to each sample, and the solvents are allowed to evaporate. The residues are resuspended in the tris-hydroxymethyl(aminomethane) buffer with 100 ul of the dioxin specific antibodies (100 ng/ml) and applied to a polystyrene microliter plate coated with trichlorodibenzodioxin(tri-CDD)-rabbit serum albumin conjugate. The retained antibodies are quantitatively determined with sheep anti-mouse IgG peroxidase and o-phenylene diamine(OPD) substrate in a dye reaction, with light absorption measured at 492 nm.

A preferred method for the immunoassay includes amplification of the peroxidase enzyme endpoint by coupling to a avidin-peroxidase/biotin-anti-mouse immunoglobulin complex. Optimal enzyme sensitivity occurs when a minimal amount of coating antigen (tri-CDD-BSA) is used. The total protein binding capacity of the plate is large so the extra unconjugated carrier protein does not degrade binding. In the preferred method, microtiter plates are coated with a tri-CDD-BSA solution by addition of about 0.2–1.0 ng of tri-CDD-BSA/well, more preferably, 0.5 ng/well. The coated plates may be dried and stored until needed.

Sample extractants in detergent solvents are mixed with the antibody buffer and transferred to antigen-coated microtiter wells. The immuno-assay is run by incubation of samples with dioxin-specific antibody at a concentration of 100 ng/ml in assay buffer for 1 hr at 37° C. The microtiter plates are washed (2×) with a 0.5% detergent (polyoxyethylene sorbitan monolaurate) wash solution.

The antibody which has partitioned between the bound dioxin antigen at the plate wall and the unbound dioxin of the extracted sample is visualized when bound to the plate-wall antigen by binding with biotinylated anti-mouse IgG immunoglobulin (approximately 1.5 ug/well). After a 45 minute incubation, avidin-peroxidase complex and biotinylated anti-mouse immunoglobulin are added and reacted for another 30 minutes. Following a 5× wash with 0.5% detergent (polyoxyethylene sorbitan monolaurate) solution, peroxide and orthophenlyenediamine (OPD) substrate are added and an initial Fast ELISA slope reading is made at 450 nm and a final Fast ELISA reading is made at 492 nm, following stop with concentrated $H_2SO_4$.

Sample values are compared to a standard curve run on each microtiter plate. The standard curve shows a 50% inhibition value between 0.1 and 0.3 ng of TCDD. Normalized data is reported as a function of gram-equivalents of starting material per well.

A serial 1:2 dilution of a 2,3,7,8-TCDD standard, in the 0.1 to 500 ppb range, is carried out at the same time on each microliter plate.

EXAMPLE 3

Evaluation

A sample concentration may be reported in TCDD equivalents based on the standard curve made by serial dilution of the 2,3,7,8-TCDD standard. The inhibition values of the undiluted sample should correspond to the inhibition values observed in the TCDD standard curve. An interference caused by matrix components which may not have been removed is indicated by discrepancies in the spiked samples. A sample measurement is invalidated if the concentration ascertained in the spiked samples does not correspond to the sample plus the added 1 or 10 ppb of the spiked sample.

EXAMPLE 4

Industrial Process Samples

A variety of industrial chemical samples derived from laboratory and technical processes were evaluated for the contamination of dioxins and dibenzofurans present by the above-described method (Table I at end of specification, page 38). The demonstration assays include five samples of various distillation residues (still bottom), 2,4,6-trichlorophenol (TCP), nitrodiphenylether, a fly ash sample, and a sample of polychlorinated biphenyl (PCB) oil from a transformer which had been involved in a fire. These samples varied considerably in kind and content of contaminants present. The contamination level of dioxins determined in samples prepared for immunoassay were compared with dioxin contamination of parallel samples assayed by gas chromatography/mass spectroscopy provided by Dr. B. Bogdoll (Anders, H., A. Buhlmann and B. Bogdoll - unpublished results). The GC/MS data was reported as the total content of all tetra-and penta-chloro congeners, and as the total contamination of the four most toxic congeners, (2,3,7,8-tetraCDD and 2,3,7,8-tetraCDF, and 1,2,3,7,8,-pentaCDD and 2,3,4,7,8-pentaCDF). Most samples contained a mixture of PCDFs and PCDDs while some contained only one of these groups of compounds. Samples were also included which had no history to suggest PCDD and PCDF contamination. These included technical grade 3,4-dichloronitro-benzene (dCNBz) which was thought to possibly cross-react with the antibodies; paraffin, which is not easily evaluated by GC/MS analysis; and HD-30 machine oil, which is a common matrix that is analyzed for PCDD.

ELISA analyses of chemical process samples required different amounts of assay material. The amount of starting material needed for determination of the 50% inhibition point of the ELISA was 1 mg for still bottom sample #1, 10 mg each for samples of PCB and TCP, and 0.4 g for the fly ash sample. These samples demonstrated a contamination level of 5,000, 500, 500, and 25 ppb levels, respectively, when expressed as equivalents of TCDD. Identical estimates of TCDD contamination were made when these samples were reanalyzed by immunoassay on a subsequent day.

Four samples which did not contain agents which would detectably inhibit the ELISA assay, the two dCNBz samples, paraffin, and machine oil, were evaluated to determine if these matrices interfered with the dioxin detection assay. Samples spiked with 1, 3, or 10 ng of TCDD, showed similar inhibition of the ELISA as would be caused by addition of similar amounts of dioxin in hexane.

EXAMPLE 5

Soil Samples

Soil samples were evaluated in several extraction procedures in an effort to determine a minimum process time which would yield high recovery of dioxins. Comparisons made on procedures using both the large-hexane-volume overnight-extraction protocol or a shorter extraction protocol with two washes of hexane showed that they each yielded greater than 90% recovery of an added radiolabeled spike of TCDD.

A rapid-extraction method that used two successive 10 ml hexane washes of the soil-sodium sulfate sample, without overnight mixing was evaluated. A lower and more variable recovery of the radiolabeled tracer was observed when the extraction method used acetonitrile:methylene chloride (1:1).

In an exemplary extraction procedure for soil samples, 10 grams of wet soil was dried by shaking with 10 grams of sodium sulfate for 1 hour. The sample was extracted with 10 ml of hexane and 5 ml of ethanol, centrifuged and the hexane layer removed by pipet. The mixture was re-extracted with 10 ml of hexane which was mixed and shaken for 15 minutes. Vigorous shaking, via a commercial paint shaker, prior to separation of the phases improved the efficacy of the extraction. The hexane layers were combined and reduced in volume in a rotary evaporator. The solvent was removed under a dry nitrogen gas stream and the residue was resuspended in 1 ml of 1:1 dichlorohexane:cyclohexane and spiked with fat blue B. The sample was applied to a column of activated carbon/glass fibers 11:9), the column was washed with dichloromethane/methanol/toluene (15:4:1) and the dioxins were recovered by reverse elution with toluene. The PCDD's (polychlorinated dibenzodioxins) and PCFD's (polychlorinated dibenzofurans) co-eluted with the colored fat blue B marker. The sample was then applied to a column of fuming sulfuric acid impregnated silica gel/silver nitrate impregnated silica gel, eluted with hexane, and evaporated. The sample was solubilized as described previously and analyzed by the immunoassay.

Soil samples spiked with 0.1-10 ppb of tetra-chlorodibenzodioxin (TCDD) typically showed 95% recovery of the TCDD spike in the extraction washes. Extracts of composite soils, taken from 0.1 and 1.0 g of soil, did not interfere with a TCDD standard curve run in buffer. When spiked soil samples were extracted by the above method and analyzed in an assay which corresponded to 0.2 g equivalents of soil/well, the immunoassay results corresponded well with the expected values for soils contaminated with dioxins in the range of 0.1-10 ppb. There was a greater correlation of immunoassay results with the spiked sample amount when 1.0 g equivalent of soil extract/well was assayed. This gave linear correlation in the 0.1 to 1.0 ppb range, although assays of samples of extracts at 10 ppb were outside of the linear region of the curve.

Multiple analyses of a soil sample were consistent when analysis was repeated over a period of several months. A selected soil sample, with an organic content of less than 1% and a sand content of 80%, was extracted overnight in hexane, followed by an overnight extraction with sulfuric acid. The sulfuric acid treatment did not interfere with the immunoassay. The inhibition curve obtained with soil extract and in spiked samples of soil extract indicated that there were detectable levels of dioxins present in the soil extracts.

Residual matrix materials of various soils may interfere with the assay. Even after extraction, some aspect of some soils continued to sequester the dioxin, making it unavailable to the dioxin-specific antibodies. Some soils have large quantities of hexane soluble organic material to which dioxin binds instead of partitioning into the solvent used in the immunoassay. With some samples, preliminary alumina or silica column chromatography did not improve the sensitivity of the assay. The total organic content of the soil or the physical properties of soil were not, alone, good indicators of whether the soil could be suitably analyzed for dioxin by immunochemical means. For some soils of low organic content, simple extraction in hexane, with sulfuric acid treatment will effectively remove interfering matter, such that immunoassay can detect dioxins contamination in the range of 1 ppb. The above-described preparative conditions are expected to be equally suitable for tissue or food samples.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

TABLE I

Chemical Samples Analyzed for Dioxins

| Sample | | | Contamination Level (ppb) | | |
|---|---|---|---|---|---|
| | | | GC/MS[b] | | Immunoassay |
| No. | Type | Size[a] (g/assay) | All tetra and penta chloro congeners | Most toxic congeners | TetraCDD equivalents |
| 1. | Still Bottom | 0.005 | 18,000 | 1725 | 5,000 |
| 2. | Still Bottom | 0.100 | 550 | 260 | 125 |
| 3. | Still Bottom | 5.000 | 1.1 | 0 | 0.6 |
| 4. | Stli Bottom | 0.100 | 50[e] | 0.3 | 250 |
| 5. | TCP | 0.025 | 2,600 | 125 | 500 |
| 6. | nitrodiphenylether | 0.100 | 21[f] | 0 | 500 |
| 7. | PCB oil[c] | 0.025 | 1,700[g] | 290 | 500 |
| 8. | Fly ash | 2.000 | 272 | 14 | 25 |
| 9. | 3,4-dCNBz | 0.050 | <1 | <1 | <20 |
| 10. | 3.4-dCNB | 0.050 | <1 | <1 | <20 |
| 11. | Paraffin | 0.050 | <1 | <1 | <20 |
| 12. | Machine oil[d] | 0.050 | <1 | <1 | <20 |
| 13. | Still Bottom | 1.000 | 19 | 7 | 25 |

[a]Largest amount of sample extract tested per well in the ELISA. Expressed in terms of mass-equivalents of starting material.
[b]GC/MS date provided by Dr. Bogdoll [12]. The "Most Toxic Congeners" numbers are the sum of 2,3,7,8-TetraCDD, 1,2,3,7,8-pentaCDD, e,3,7,8-TetraCDF, and 2,3,7,8-pentaCDF.
[c]From a transformer that had burned.
[d]HD-30.
[e]Sample contained dioxins only.
[f]Sample also contained 18,000 ppb of TriCDD.
[g]Sample contained furans only.

We claim:

1. A method of preparing samples containing organic-extractable materials, said method to precede methods for detecting levels of dioxins and dibenzofurans in prepared samples, said method comprising the steps of:
   a. providing a sample with organic-extractable materials;
   b. suspending the sample in strong acid to obtain a suspension;
   c. extracting the suspension of step (b) by reflux with an organic solvent to obtain a raw extract;
   d. separating a fraction of dioxins or dibenzofurans from the raw extract by reactive chromatography; and
   e. solubilizing the dioxin or dibenzofuran fraction in step (d) in an aqueous buffer solution to obtain an aqueous dioxin or dibenzofuran fraction;
   wherein the aqueous dioxin fraction is substantially free of organic-extractable materials and suitable for assay by immunodiagnostic methods.

2. The method according to claim 1 wherein the chromatography step uses a matrix or matrices selected from the group consisting of carbon-glass, activated silica, fuming sulfuric acid-silica, silver nitrate silica and acid alumina.

3. The method according to claim 1 wherein at least one dye, having a similar absorption and elution behavior as the dioxin or dibenzofuran fraction, is employed to monitor said chromatography step.

4. The method according to claim 1 wherein step (e) comprises adding at least one detergent to the dioxin or dibenzofuran fraction.

5. A method for quantitative immunodetection of dioxins or dibenzofurans in samples containing other organic-extractable materials, said method comprising the steps of
   a. providing a sample containing other organic-extractable materials;
   b. preparing a raw extract by
      i) acid digestion with oleum to obtain a suspension followed by
      ii) extraction of the suspension with an organic solvent;
   c. separating a dioxin fraction from the raw extract by activated carbon and reactive chromatography;
   d. solubilizing the dioxin fraction in an aqueous buffer solution; and
   e. determining the amount of dioxin in the solubilized dioxin fraction by an immunoassay procedure.

6. The method according to claim 5 wherein said immunoassay procedure is carried out in a microtiter plate in which about 1–10 ng of dioxin coats each immunoreactive well.

7. The method according to claim 5 wherein step (e) employs at least one dioxin-specific monoclonal antibody.

8. The method according to claim 7 wherein said immunoassay procedure is carried out in a microtiter plate in which about 0.2–1.0 ng dioxin coats each immunoreactive well.

9. The method according to claim 7 wherein the dioxin-specific monoclonal antibody is selected from hybridomas of the group consisting of: DD-1, DD-3, DD-4, DD-5, and DD-6, with ATCC Accession Nos. (HB 9741), (HB 9742), (HB 9743), (HB 9743), and (HB 9745), respectively; or mixtures thereof.

10. The method according to claim 5 wherein the aqueous buffer of step (d) comprises at least one detergent, wherein the detergent is in a concentration range of about 0.01–2% by weight.

11. The method according to claim 10 wherein the detergent is in the concentration range of 0.1–0.4% by weight and is selected from the group consisting of isooctylphenoxypolyethoxyethanol, polyoxyethylene sorbitan monolaurate, polyoxyethylene stearyl ether, polyoxyethylene lauryl ether, octylphenol ethoxylate and combinations thereof.

12. The method according to claim 5 wherein the immunoassay of step e is a competitive immuno-binding procedure.

13. The method according to claim 12 wherein sensitivity of the competitive immuno-binding procedure is amplified with avidin-biotin linkages.

14. The method according to claim 5 wherein step d is performed with ultrasonic mixing.

* * * * *

UNITED STATES PATENT AND TRADEMARK OFFICE
CERTIFICATE OF CORRECTION

PATENT NO. : 5,429,925
DATED : July 4, 1995
INVENTOR(S) : Martin Vanderlaan, et al.

It is certified that error appears in the above-identified patent and that said Letters Patent is hereby corrected as shown below:

Column 5, line 10, change "Inhibition" to --inhibition--.

Column 12, line 9, change "phenlyenediamine" to --phenylenediamine--.

Column 13, line 10, change "5,000, 500 and 500" to --5,000, 500, 50,--.

Column 16, line 47, before "), and" change "9743" to --9744--.

Signed and Sealed this

Thirty-first Day of October 1995

Attest:

BRUCE LEHMAN

Attesting Officer

Commissioner of Patents and Trademarks